United States Patent
De Santis et al.

(10) Patent No.: US 7,425,317 B2
(45) Date of Patent: Sep. 16, 2008

(54) AVIDIN DIMERS EFFECTIVE IN INCREASING THE CONCENTRATION OF RADIOACTIVE BIOTIN IN PRETARGETED RADIOIMMUNOTHERAPY

(75) Inventors: Rita De Santis, Pomezia (IT); Ragnar Lindstedt, Pomezia (IT); Carlo Nuzzolo, Pomezia (IT)

(73) Assignee: Sigma-Tau Industrie Farmaceutiche, Rome (IT)

( * ) Notice: Subject to any disclaimer, the term of this patent is extended or adjusted under 35 U.S.C. 154(b) by 308 days.

(21) Appl. No.: 10/506,159

(22) PCT Filed: Mar. 6, 2003

(86) PCT No.: PCT/IT03/00135

§ 371 (c)(1),
(2), (4) Date: Sep. 1, 2004

(87) PCT Pub. No.: WO03/075960

PCT Pub. Date: Sep. 18, 2003

(65) Prior Publication Data

US 2005/0106102 A1    May 19, 2005

(30) Foreign Application Priority Data

Mar. 8, 2002 (IT) .......................... RM2002A0128

(51) Int. Cl.
*A61K 51/00* (2006.01)
*A61M 36/14* (2006.01)

(52) U.S. Cl. ................... 424/1.49; 424/1.11; 424/1.65; 206/223; 206/569

(58) Field of Classification Search ................ 424/1.11, 424/1.49, 1.65, 1.69, 1.73, 9.1, 78.01, 9.3, 424/9.4, 9.5, 9.6, 9.7, 9.8; 536/1.11; 206/223, 206/569, 570

See application file for complete search history.

(56) References Cited

U.S. PATENT DOCUMENTS 4,687,732 A * 8/1987 Ward et al. ...................... 435/6
5,482,698 A * 1/1996 Griffiths ..................... 424/1.41

OTHER PUBLICATIONS

Chinol et al, "Biochemical modifications of avidin improve pharmacokinetics and biodistribution, and reduce immunogenicity", British Journal of Cancer, vol. 78, No. 2, Jul. 1998, pp. 189-197.
Reznik et al, "Streptavidins with intersubunit crosslinks have enhanced stability", Nature Biotechnology, Nature Publishing, US, vol. 14, Aug. 1998, pp. 1007-1011.
Chinol et al—Biodistribution in tumour-bearing mice of Two 90Y-labelled biotins using three-step tumour targeting, Nuclear Medicine Communications, 1997, 18, pp. 176-182.
Cremonesi et al, "Three-step radioimmunotherapy with yttrium-90 biotin: dosimetry and pharmacokinetics in cancer patients", European Journal of Nuclear Medicine, vol. 26, No. 2, Feb. 1999, pp. 110-120.
Hart et al, "HPMA copolymer-modified avidin: Immune response", Journal of Biomaterials Science, Polymer Edition, vol. 11, No. 1, 2000, pp. 1-12.

* cited by examiner

*Primary Examiner*—D. L Jones
(74) *Attorney, Agent, or Firm*—Nixon & Vanderhye P.C.

(57) ABSTRACT

Dimers of avidin and streptavidins (diavidins) are described wherein the linker is suberate, which in turn, is bound to different functional groups (—NH2 o-COOH) of avidin. As compared to avidin, the diavidins have shown the ability to increase the amount of labelled biotin on the target, when used in an in vitropretargeting test using supported human tenascin, the biotinylated anti-tenascin monoclonal antibody (Mab-B), avidin/diavidin, and biotin-3H. The use of such diavidins is also described in cancer diagnosis and anticancer therapy based on the three-step pretargeted radioimmunotherapy procedure.

4 Claims, 6 Drawing Sheets

Separation of Diavidin 1, 2 and 3 by gel filtration

AVIDIN DIMERS EFFECTIVE IN INCREASING THE CONCENTRATION OF RADIOACTIVE BIOTIN IN PRETARGETED RADIOIMMUNOTHERAPY This application is the U.S. national phase of international application PCT/IT03/00135 filed 6 Mar. 2003 which designated the U.S. and claims benefit of IT RM2002A000128, dated 8 Mar. 2002, the entire content of which is hereby incorporated by reference.

The invention described herein relates to derivatives of avidin which are useful in the diagnosis and treatment of tumours, and particularly in the so-called three-step pretargeting method.

TECHNICAL FIELD

The invention described herein relates to modified avidins which are useful for use in human and animal diagnosis and therapy, and particularly for the diagnosis and treatment of pathological conditions such as tumours.

The invention described herein relates to the technical field of the preparation of medicaments and diagnostic means and provides compounds, methods for their preparation, methods for their use, and compositions containing them which are suitable for industrial application in the pharmaceutical field.

The invention described herein provides compounds, compositions and methods which are useful in diagnostic and therapeutic medicament, as image acquisition techniques and treatments for pathological conditions of organs and tissues.

In particular, but not exclusively, the present invention relates to the field of tumour therapy by means of radiopharmaceuticals.

BACKGROUND TO THE INVENTION

Tumour therapy is mainly implemented by means of the use of substances aimed at killing the tumour cells. This can be achieved with cytotoxic substances which have to enter the tumour cell in order to exert their full effect, or by means of treatment of the tumour cells with radiation with sufficient energy to kill the cell. In both cases, there is the problem of delivering the substance as selectively as possible to the target cell, so as to avoid possible damage to the surrounding healthy cells. In the case of radiopharmaceuticals, i.e. of substances bearing radioactive portions, the problem of selectively delivering the active part (that is to say, the radioactive portion) to the tumour target, avoiding the spread of radionuclide in the body or in the healthy cells surrounding the tumour, is of particular concern.

One particularly effective method for tumour detection and therapy is described in patent EP 0 496 074. The protocol of this patent has been applied to the so-called Pretargeted Antibody-Guided Radioimmunotherapy (PAGRIT) of brain tumours. In this method, avidin is injected into the human subject, after the biotinylated anti-tenascin monoclonal antibody (Mab-B), to remove any free Mab-B, not bound to the tumour, from the bloodstream by forming complexes with it that are effectively eliminated by the liver (chase effect). An infusion of streptoavidin is then administered for the purposes of obtaining better avidination of the tumour compared to that obtainable with avidin, whose permanence in the blood is too short compared to that of streptoavidin.

Though the system has shown positive clinical responses (Cremonesi, M. et al., 1999; Paganelli, G. et al., 1999; Paganelli, G. et al., 2001), one major limiting factor consists in the strong immune response caused by streptoavidin (Paganelli, G. et al., 1997). For the purposes of overcoming these two obstacles, i.e. the high degree of immunogenicity of streptoavidin and the rapid clearance of avidin, avidins have been used which are chemically modified by covalently binding polyoxyethylene glycol (PEG) chains to avidin, with various levels of derivatisation based on the use of straight or branched PEGs of different molecular weights. Preliminary studies have revealed that, with the increase in the degree of functionalisation of avidin with PEG (hereinafter referred to as pegilation), there is an increase in the plasma half-life of avidin, a reduction in immunogenicity, and an improvement in the specific biodistribution of the substance in relation to the tumour.

Since the ability of avidin-PEG to bind to Mab-B biotin is reduced by pegilation, the result is a reduction in the potency of the derivatives (Chinol, M. et al., 1998).

A solution to this problem has been proposed in patent application WO 94/23759, filed in the name of Immunomedics, where avidin multipolymers are described based on the chemical derivatisation of high-molecular-weight molecules, preferably greater than 5,000 Da, such as dextrane, proteins and polycarboxylic acids. But none of the five multimers effectively described in the patent has been characterised in terms of its potency of action in the pretargeting procedure or in other procedures.

As demonstrated in the invention described herein, the general concept of multimerisation (also including dimerisation), given in the above-mentioned patent application WO 94/237599, fails to provide complete and sufficient instructions for the average technician in finding a generic avidin multimer capable of fulfilling the necessary requirements in the application of the three-step pretargeting method. In fact, different diavidins, obtained using different bifunctional cross-linkers, though possessing the same ability to bind free biotin, differ in their potency when assayed in vitro in three-step pretargeting, to the extent that, in certain cases, they prove to be completely inefficacious.

This observation indicates that the multimerisation of avidin does not automatically produce useful functional products, but that biological characterisation is necessary for the choice of a potentiated molecule suitable for pretargeting.

SUMMARY OF THE INVENTION

It has now been found that by binding two molecules of avidin with a bifunctional linker, capable of binding the amino and/or carboxy groups of avidin, selected from disuccinimidyl suberate (dimer hereinafter referred to as diavidin 1) and PEG diamine with molecular weight 3400 (dimer hereinafter referred to as diavidin 2), two avidin dimers are obtained which fulfil the requisites for use in the tumour treatment method known as PAGRIT.

Thus the objects of the invention described herein are an avidin dimer in which two molecules of avidin are bound via the —NH$_2$ groups by means of a suberate and an avidin dimer in which two molecules of avidin are bound via the —COOH groups by means of polyethylene glycol with a molecular weight of 3400.

Further objects of the invention described herein are pharmaceutical and/or diagnostic compositions containing the above-mentioned diavidins.

Other objects of the present invention are the use of diavidins as medicaments or diagnostic agents for pathological conditions of organs and tissues, and particularly for the preparation of medicaments useful for the therapy or diagnosis of tumours.

These and other objects related to the present invention will be illustrated in detail here below, also by means of experimental examples.

DETAILED DESCRIPTION OF THE INVENTION

Figure 1:
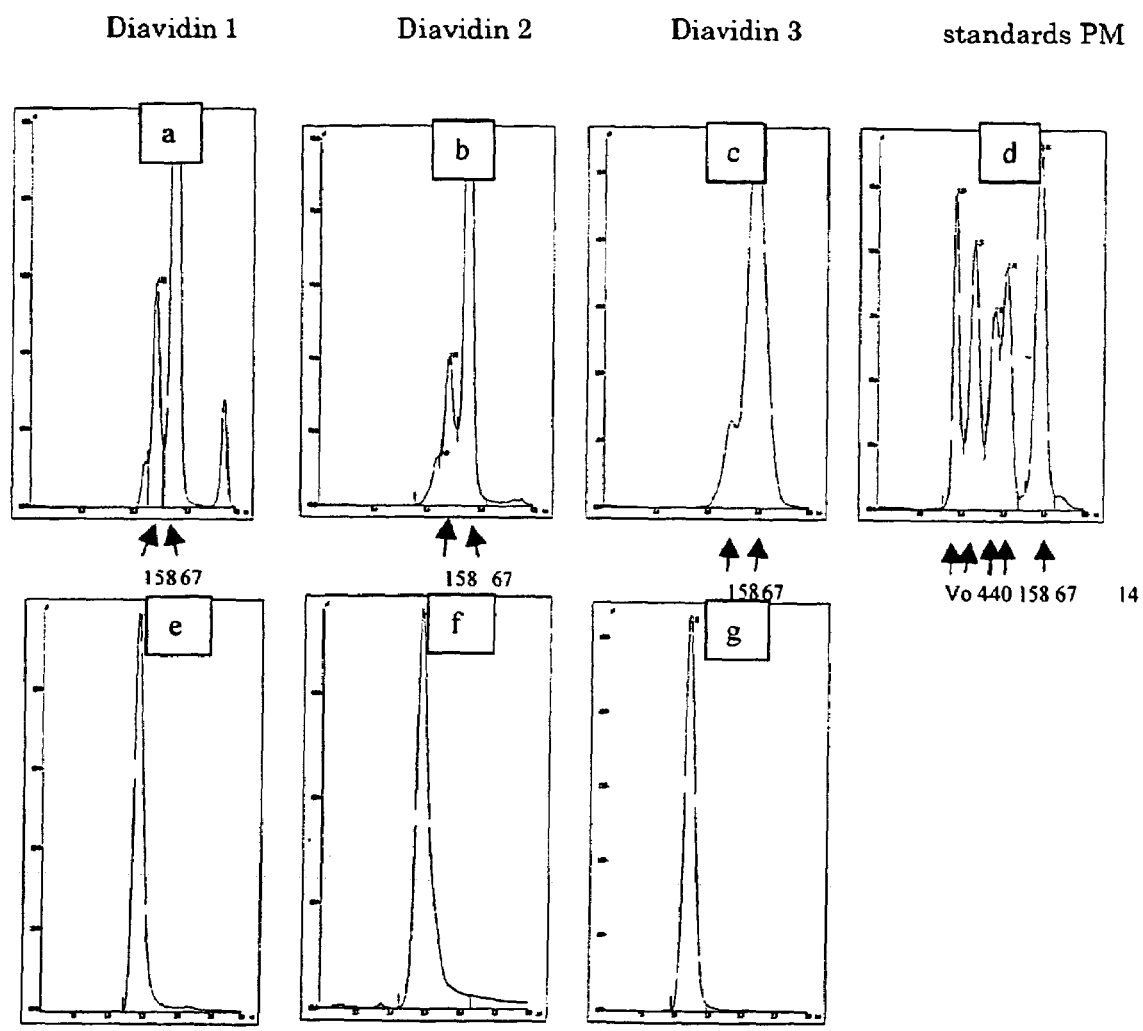
FIG. 1 shows the chromatographic profile of diavidin 1 separated by gel filtration (a), diavidin 2 separated by gel filtration (b), diavidin 3 separated by gel filtration (c), protein standards for calibration (d), purified diavidin 1 (e), purified diavidin 2 (f) or purified diavidin 3 (g).

As intended in the present invention, avidin means both avidin and streptavidin, but the case in which streptavidin is used as particular embodiment of the present invention, this fact will be specified.

Diavidin 1 was prepared by reacting avidin with disuccinimidyl suberate (DSS), having N-hydroxysuccinimidyl (NHS ester) as the active ester, DSS being a homobifunctional cross-linker reactive in binding the —$NH_2$ group of avidin.

Diavidin 2 and diavidin 3 (negative control) were generated using PEG diamine (PEG($NH_2$)$_2$) with a molecular weight of 3400 and polyethylene glycol-disuccinimidylpropionic acid [PEG (SPA)$_2$] with a molecular weight of 3400, respectively, as homobifunctional cross-linkers.

Due to the slower elimination of streptavidin compared to avidin from the circulation, distreptavidin are a particular embodiment of the present invention. The longer half-life is crucial to achieve the maximum increase in efficiency of avidins. The protocol for streptavidin cross-linking was similar to the one used for diavidin 1 production.

The pharmaceutical or diagnostic compositions according to the invention described herein contain at least one of the diavidins described here. The diavidin will be in a mixture with suitable vehicles and/or excipients commonly used in pharmacy, such as those described in "Remington's Pharmaceutical Sciences Handbook", latest edition. The compositions according to the present invention will contain an efficacious amount of diavidin.

Preferred examples of pharmaceutical compositions are those that permit parenteral and locoregional administration. Pharmaceutical compositions suitable for the purpose are solutions, suspensions, or lyophilised forms to be reconstituted at the time of use.

As regards the use of the diavidins according to the present invention, these are particularly suitable for the preparation of medicaments or diagnostic means for the diagnosis or therapy of pathological conditions of tissues, such as, for example, tumours, by means of the technique known as pretargeting with antibodies, and for this reason are also suitable for in-vitro pretargeting techniques. In one realisation by way of an example, the pretargeting technique is implemented with a biotinylated anti-tenascin antibody, preferably a monoclonal antibody.

Suitable forms for the industrial application of the present invention are also kits for diagnosis or therapy, particularly the radiotherapy of tumours, such as, for example, is described in EP 0 496 074, in the study by Paganelli, Chinol et al. published in the *European Journal of Nuclear Medicament* Vol. 26, No 4, April 1999; 348-357, U.S. Pat. No. 5,968, 405 and related literature.

A further object of the invention described herein is a kit for tumour therapy or diagnosis, particularly by means of radioactivity, for example, with the pretargeting method, preferably three-step, characterised in that at least one of the components of said kit contains a diavidin. In said kit, one preferred biotinylated antibody is an anti-tenascin antibody, and even more preferably a monoclonal antibody.

The following examples further illustrate the invention.

EXAMPLE 1

Diavidin 1

1 ml of avidin solution, 300 μM in PBS, pH 7.4, was mixed with 25 μl of DSS (from Pierce) 25 mM in DMSO (avidin: DSS ratio: 1:2). The mixture was incubated for 2 hours at 0° C. before blocking the reaction with 50 μl of Tris 1M, pH 8.0. The choice of the aforesaid reaction ratio was based on preliminary tests using ratios from 1:1 to 1:10.

The reaction scheme is as follows:

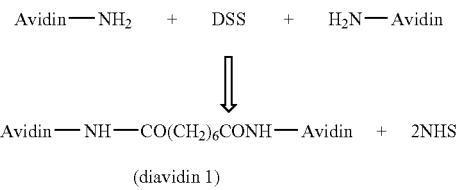

(diavidin 1)

EXAMPLE 2

Diavidin 2

1 ml of avidin, 450 μM in PBS, pH 7.4, was mixed with 120 μl of PEG ($NH_2$)$_2$ (from Shearwater Corp.) 9 mM in $H_2O$ and 50 μl of 1-(3-dimethylaminopropyl)-3-ethyl (EDAC) 260 mM in DMSO (avidin:PEG ratio: 1:2.5 approx.) and left to react for 2 hours at ambient temperature. At the end of this period 50 μl of Tris 1 M, pH 8.0, were added and the mixture was submitted to gel filtration. The avidin:PEG ratio was investigated over a range from 1:1 to 1:10 at a reaction pH from 4.0 to 8.0. The value of the PEG:avidin ratio in the purified diavidin 2 end product was 0.9, using the method described by Sims et al., 1980. In brief diavidin 2 was diluted to 300 μM in water, 250 μl of 5% $BaCl_2$ in HCl 1N were added to a volume of 1 ml, and then 250 μl of a solution prepared by mixing 1.27 g of $I_2$ in 100 ml of KI 2%. The mixture was incubated for 15 minutes and then the absorbance reading was taken at 535 nm. The standard curve was obtained with PEG ($NH_2$)$_2$.

The reaction scheme for diavidin 2 is as follows

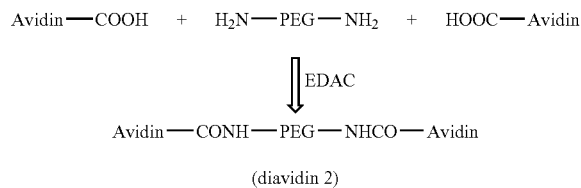

(diavidin 2)

EXAMPLE 3

Diavidin 3

1 ml of avidin 150 μM in PBS, pH 7.4, was mixed with 20 μl of PEG disuccinimidyl-propionate (SPA-PEG-SPA) 20 mM in $H_2O$ (avidin:PEG ratio: 1:3.5) and left to react for 2 hours at 0° C. The reaction ratio was selected on the basis of preliminary tests conducted with ratios ranging from 1:2 to 1:10. The value of the PEG:avidin ratio in the purified dimer, as determined using the method developed by Sims et al., as above, was 3:1. The reaction scheme is as follows:

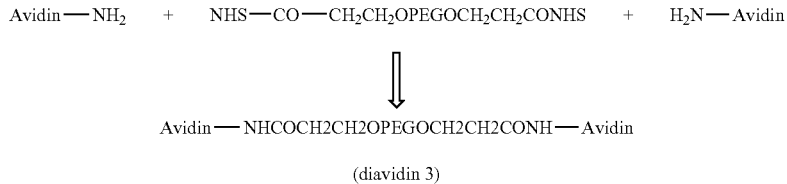

(diavidin 3)

The diavidin yield in the three reactions described in examples 1, 2 and 3 was approximately 20-30%. On increasing the amount of the three linkers in the reactions, greater final amounts of avidin oligomers were obtained (trimer, etc., not shown), with difficulties in chromatographic separation as a result. The reaction mixtures were analysed on a Superdex 200-10/30 gel filtration column, while the purification of the products was done on a Superdex 200-16/60 column. The chromatography profiles of the reaction mixtures for diavidin 1, 2 and 3 are shown in FIGS. 1a, b and c, respectively. The molecular weights of a series of standard proteins (calibration) are indicated at the respective elution times. The calibration of the column is shown in FIG. 1d: dextrane blue (Vo), ferritin (444 KDa), aldolase (158 KDa), albumin (67 KDa), and ribonuclease (14 KDa) were used.

The purified avidin dimers are presented in FIGS. 1e, f and g. The samples were separated on Superdex 200-10/15 at a flow rate of 0.5 ml/min. (a-d) and 1 ml/min (e-g) in PBS on the Jasco HPLC system connected up to a 280 nm spectrophotometer.

EXAMPLE 4

Distreptavidin 1 ml of streptavidin (300 μM in PBS, pH 7.4) was mixed with 25 μl of DSS (25 mM in DMSO) at an streptavidin:DSS ratio of 1:2 and incubated for 2 hrs at 0° C. before the reaction was quenched with 50 μl 1M TRIS, pH 8.0. A total of 4 reaction conditions were tested with a ratio of streptavidin: DSS ranging from 1:1 to 1:10. We selected the above described ratio of 1:2.

The reaction scheme is analogous to the ones reported in the previous Examples.

Figure 5:
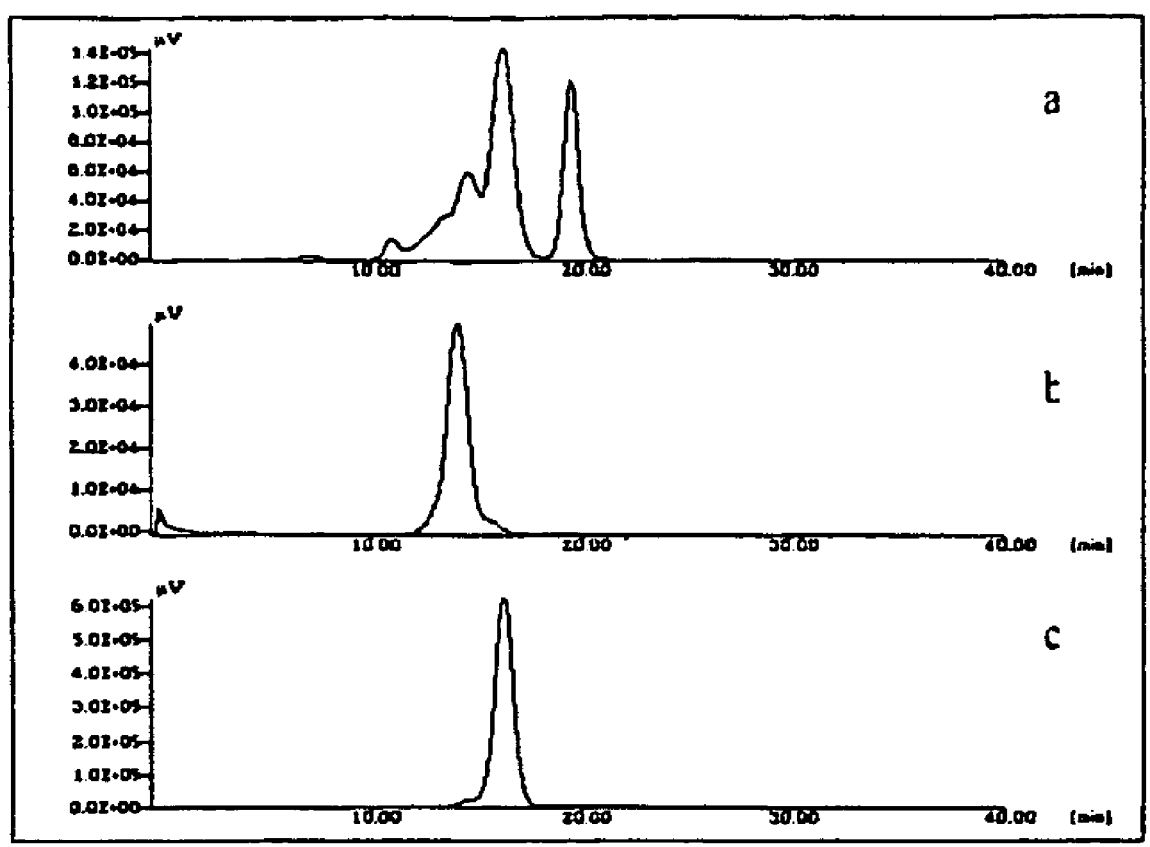
FIG. 5 shows the chromatographic profile of the crosslinking mixture at the end of the reaction (a), purified distreptavidin (b) or streptavidin (c).

The chromatographic profile of the crosslinking mixture at the end of the reaction for distreptavidin is shown in the FIG. 5a. The purified distreptavidin is shown in the FIG. 5b and streptavidin in 5c. The samples were analyzed on a Superdex200 10/15column at a flow of 1 ml/min in PBS on a Jasco HPLC system connected to a spectrophotometer measuring the absorbance at 280 nm.

Determination of the Ability of Diavidins to Bind Biotin

To compare the ability of avidin and diavidin to bind biotin the HABA (4-hydroxy-azobenzene-2'-carboxylic acid) method was used. Avidin and diavidins were all in a concentration corresponding to 3 μM of 67 KDa avidin monomer, in 0.1 M phosphate, 0.4 mM HABA at pH 7.0. Biotin dissolved in phosphate was then added to a final concentration ranging from 0 to 20 μM and the absorbance was measured at 500 nm.

The ability to bind biotin was assessed as the biotin concentration necessary to displace 50% of bound HABA.

Figure 2:
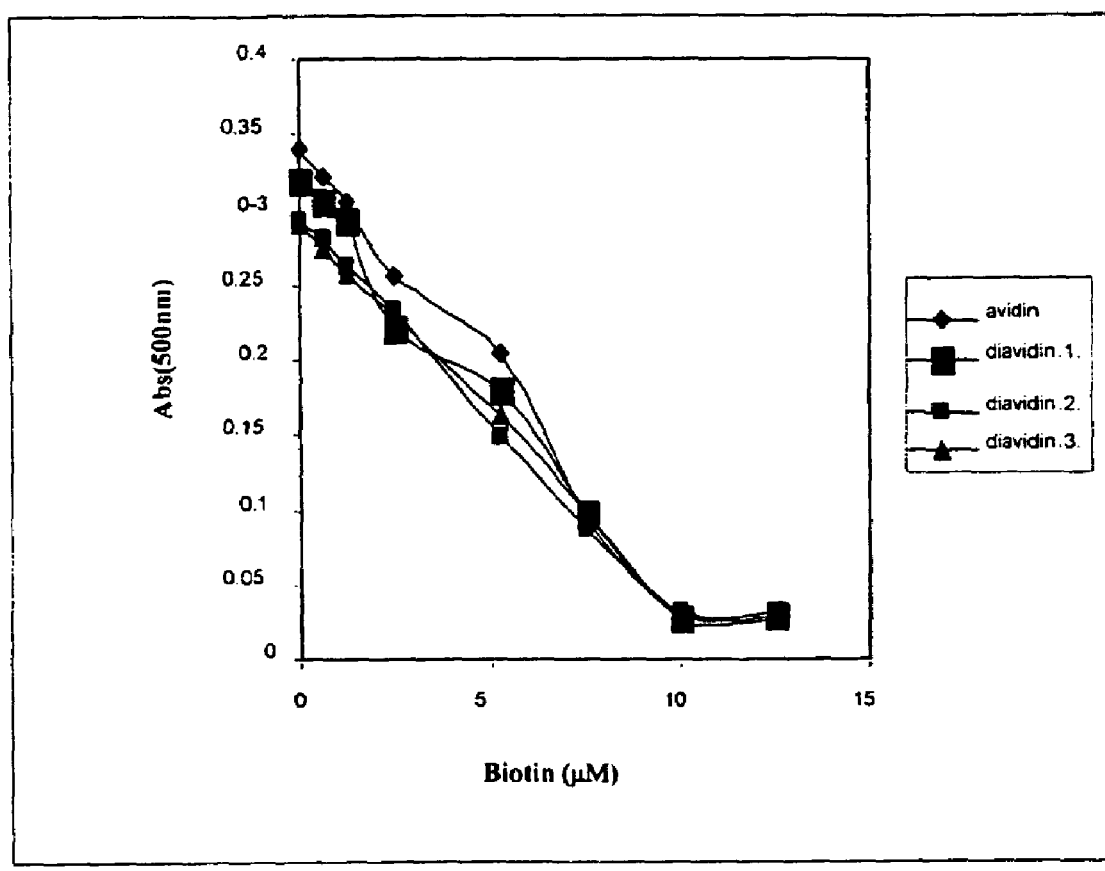
FIG. 2 shows the ability of avidin, diavidin 1, diavidin 2 or diavidin 3 to bind biotin by the HABA (4-hydroxy-azobenzene-2'-carboxylic acid) method.

Biotin 5 μM approx. was capable of displacing 50% of HABA both with avidin and with the three diavidins (FIG. 2), from which it can be deduced that the diavidins conserve the total number of binding sites after the cross-linking. The biotin-binding properties of diavidin are comparable to those of avidin.

In-Vitro Pretargeting Assays

Figure 3:
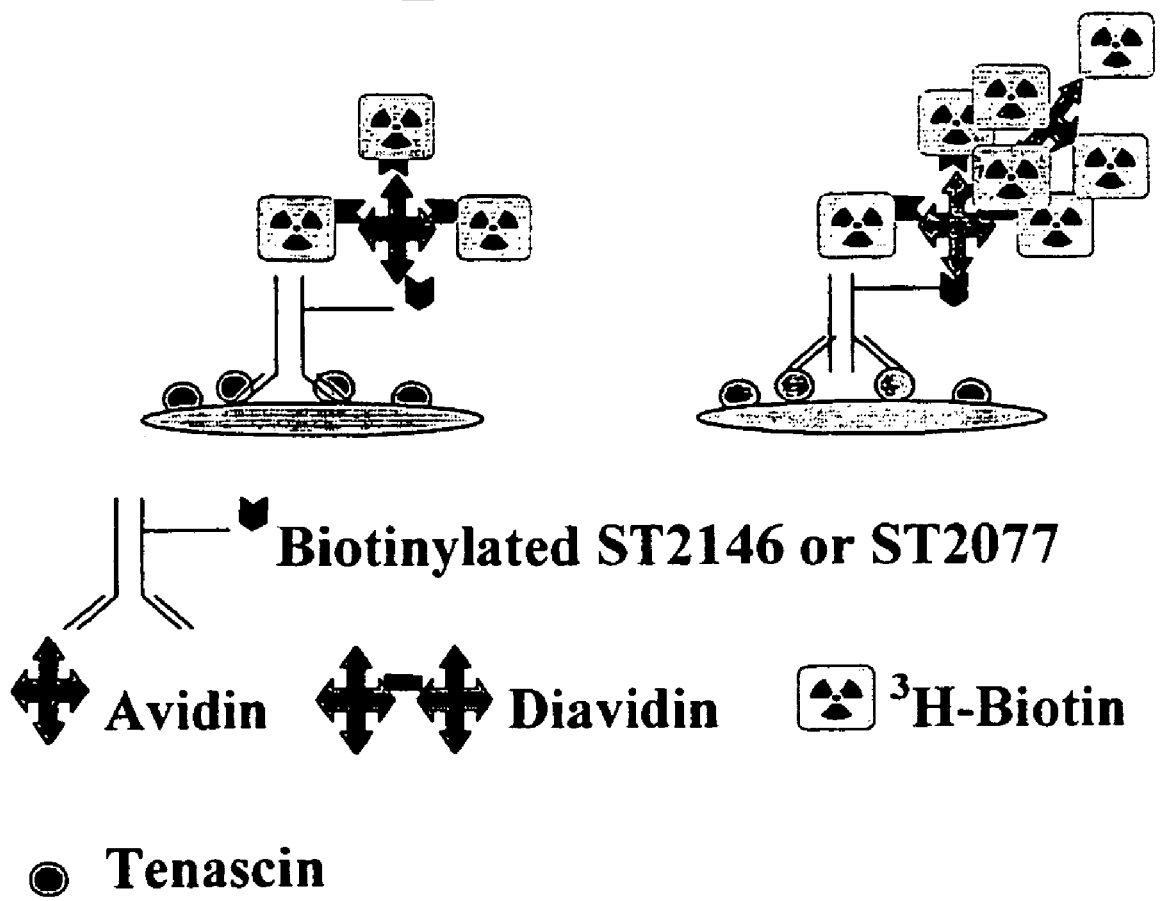
FIG. 3 illustrates schematically an in vitro pretargeting assay.

To test the ability of diavidins to increase the amount of radiolabelled biotin binding to tenascin via the biotinylated anti-tenascin monoclonal antibody (Mab-B), the in-vitro pretargeting assay schematically illustrated in FIG. 3 was used.

Figure 4:
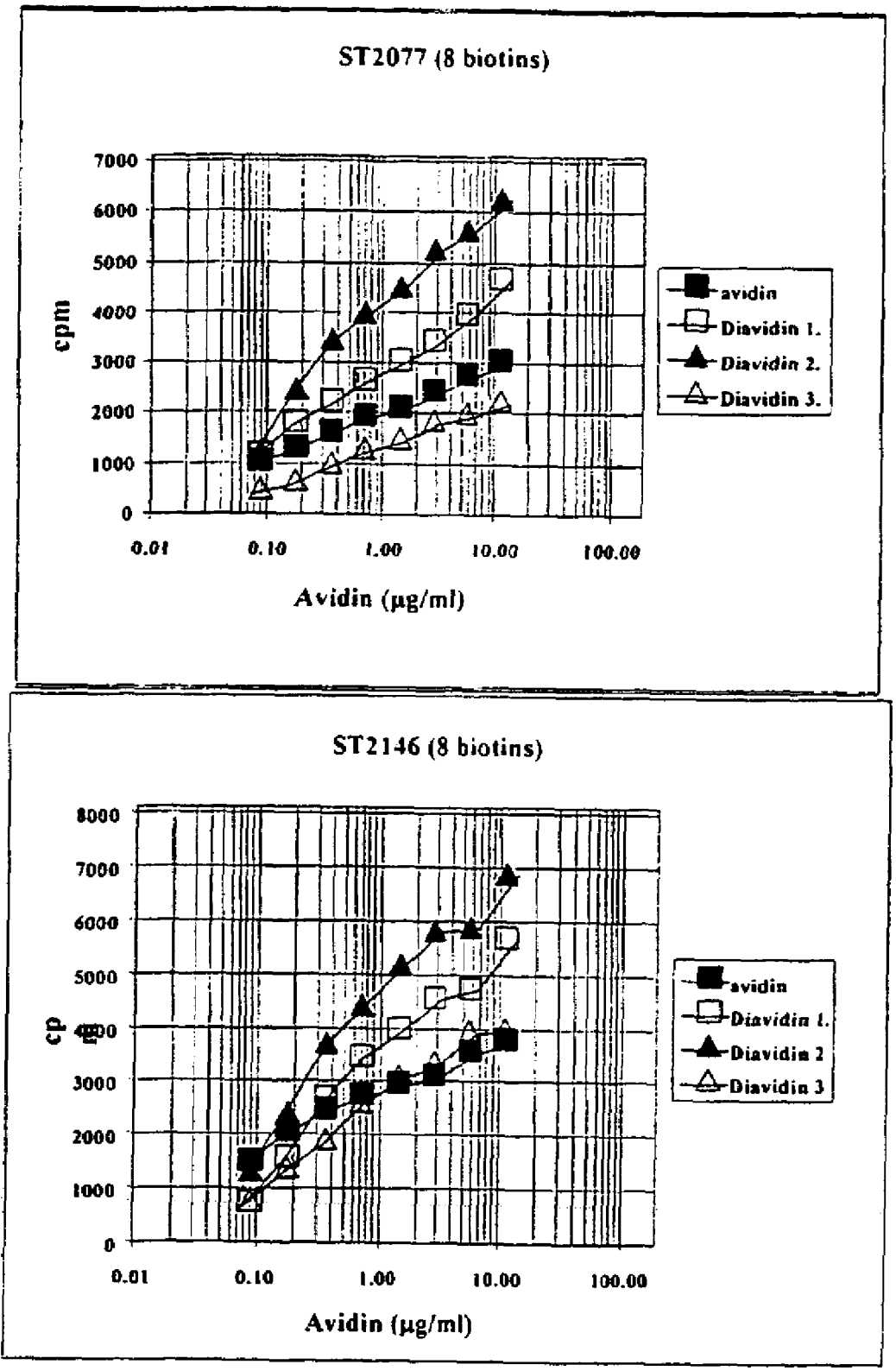
FIG. 4 shows the in vitro pretargeting assay with avidin, diavidin 1, diavidin 2 or diavidin 3 binding either to monoclonal antibody ST2146 or ST2077.

In brief, a 96-well plate was adsorbed with 0.5 μg/well of human tenascin (Tn-C) for 16 hours at 4° C. After three washings with PBS and 0.1% Tween 20. the residual adsorbent sites in the wells were blocked with PBS, 2% BSA 2% and 0.1% Tween 20, for 1 hour at ambient temperature. Two biotinylated anti-tenascin monoclonal antibodies (ST2146 or ST2077) were then incubated for 2 hours in the wells, at the saturating concentration of 10 μg/ml. After washing as above, avidin or diavidin were incubated in duplicate in the wells at increasing concentrations. Lastly, a saturating amount of 5 pmol of biotin-$^3$H (1.6 TBq/mmol) was incubated for 1 hour in each well. After washings, the plate reading was taken in a β-counter. As shown in FIG. 4, for the two MAbs used, diavidin 1 and diavidin 2 produce an increase in bound biotin compared to avidin; diavidin 3 shows no increase with MAb ST2146 or shows a reduction of binding ability with MAb ST2077.

As compared to avidin, diavidin 2 at the concentration of 2.5 μg/ml shows an increase in the amount of bound biotin-$^3$H by a factor of 2.1 (mean of 3 experiments) with Mab ST2077. For diavidin 1 the increase was by a factor of 1.6 (mean of 6 experiments), whereas for diavidin 3 the binding ability was lower (90%) compared to the avidin monomer.

From these experiments it can be concluded that both the length of the linker and the binding sites involved in the diavidin dimer affect the activity of the dimer in pretargeting mediated by biotinylated antibodies.

Figure 6:
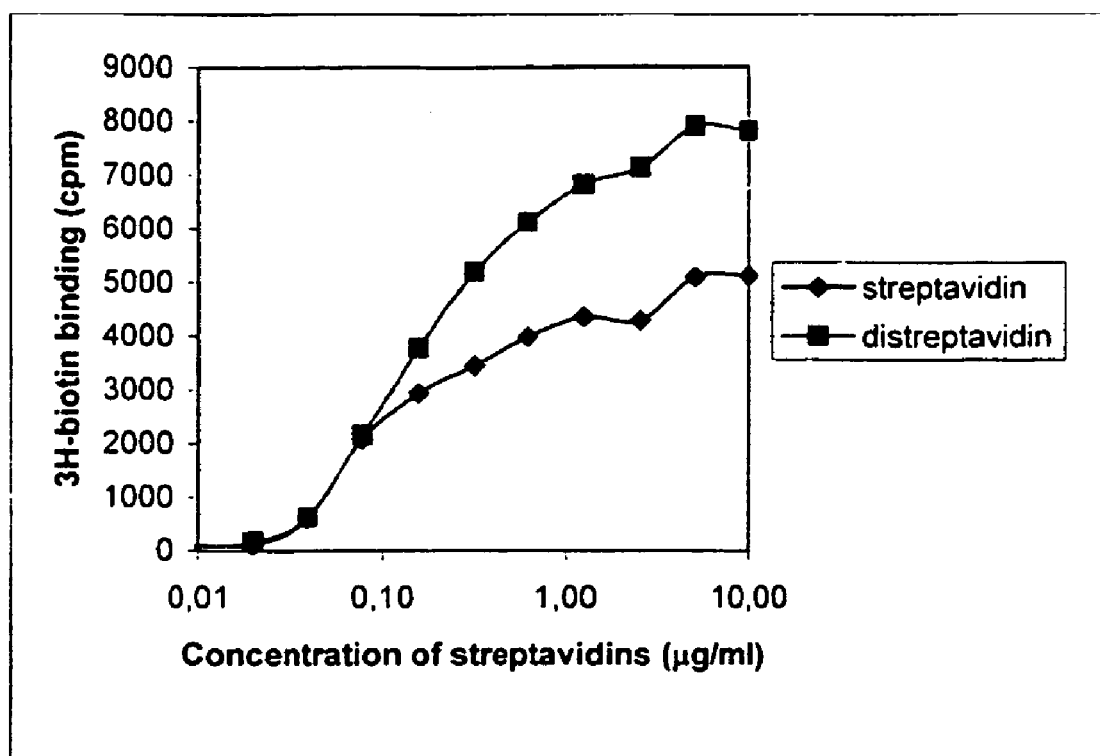
FIG. 6 shows streptavidin or distreptavidin binding to biotin.

Distreptavidin proved to be more potent than streptavidin in vitro as shown in the FIG. 6.

Microtiter 96 well plates were coated with 0.5 µg/well of human TnC for 16 hrs at 4° C., washed 3 times with PBS, 0.1% Tween-20 and then blocked for unspecific binding with PBS/2%BSA/0.1%Tween-20. The biotinylated anti-TnC antibody ST2146 was added at a concentration of 10 µg/ml for 2 hrs. The wells were washed 3 times with PBS/Tween-20 and thereafter streptavidin or distreptavidin were added at the indicated concentrations. Finally, 5 pmol 3H-biotin (1.6 TBq/mmol) were added, the wells incubated for 2 hrs, washed and counted in a β-counter.

As shown in FIG. 6 distreptavidin mediates increased binding of radiolabeled biotin compared to streptavidin.

REFERENCES

Chinol M., Casalini P., Maggiolo M., Canevari S., Omodeo E. S., Caliceti P., Veronese F. M., Cremonesi M., Chiolerio F., Nardone E., Siccardi A. G., Paganelli G. *Biochemical modifications of avidin improve pharmacokinetics and biodistribution, and reduce immunogenicity. British Journal of Cancer* 78(2): 189-197, 1998.

Cremonesi M., Ferrari M., Chinol M., Stabin M. G., Grana C., Prisco G., Robertson C., Tosi G., Paganelli G. *Three-step radioimmunotherapy with yttrium-90 biotin: dosimetry and pharmacokinetics in cancer patients. Eur J Nucl Med* 26(2):110-120, 1999.

Paganelli G., Chinol M., Maggiolo M., Sidoli A., Corti A., Baroni S., Siccardi A G. *The three-step pretargeting approach reduces the human anti-mouse antibody response in patients submitted to radioimmunoscintigraphy and radioimmunotherapy. Eur J Nucl Med* 24:350-351, 1997.

Paganelli G., Grana C., Chinol M., Cremonesi M., De Cicco C., De Braud F., Robertson C., Zurrida S., Casadio C., Zoboli S., Siccardi A. G., Veronesi U. *Antibody-guided three step therapy for high grade glioma with yttrium-90 biotin. Eur J Nucl Med* 26(4):348-357, 1999.

Paganelli G., Bartolomei M., Ferrari M., Cremonesi M., Broggi G., Maira G., Sturiale C., Grana C., Prisco G., Gatti M., Caliceti P., Chinol M. *Pre-targeted locoregional radioimmunotherapy with $^{90}$Y-biotin in glioma patients: Phase I study and preliminary therapeutic results. Cancer Biother & Radiopharm* 16(3):227-235, 2001.

Sims G. E. S. and Snape T. J. *A method for estimation of polyethylene glycol in plasma protein fractions. Anal Biochem* 107:60-63, 1980.

The invention claimed is:

1. Kit for radiotherapy or diagnosis of tumours, comprising a biotinylated anti-tenascin antibody and an avidin dimer, in which two molecules of avidin are bound via —NH$_2$ groups by crosslinking with disuccinimidyl suberate.

2. Kit for radiotherapy or diagnosis of tumours, comprising a biotinylated anti-tenascin antibody and an avidin dimer, in which two molecules of avidin are bound via —COOH groups by crosslinking with polyethylene glycol diamine with a molecular weight of 3400.

3. The kit of claim 1, wherein the avidin is streptavidin.

4. The kit of claim 2, wherein the avidin is streptavidin.

* * * * *